(12) United States Patent
Zhou et al.

(10) Patent No.: US 9,487,747 B2
(45) Date of Patent: Nov. 8, 2016

(54) CELL CULTURE DEVICE

(75) Inventors: Guangbin Zhou, Tokyo (JP); Taizo Miyazaki, Tokyo (JP); Ryota Nakajima, Tokyo (JP); Toyoshige Kobayashi, Tokyo (JP); Shizu Matsuoka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 245 days.

(21) Appl. No.: 14/124,754

(22) PCT Filed: Jun. 5, 2012

(86) PCT No.: PCT/JP2012/064466
§ 371 (c)(1),
(2), (4) Date: Jan. 16, 2014

(87) PCT Pub. No.: WO2012/169493
PCT Pub. Date: Dec. 13, 2012

(65) Prior Publication Data
US 2014/0186941 A1    Jul. 3, 2014

(30) Foreign Application Priority Data

Jun. 10, 2011 (JP) ................................ 2011-130197
Aug. 23, 2011 (JP) ................................ 2011-181369

(51) Int. Cl.
*C12M 3/00*    (2006.01)
*C12M 1/00*    (2006.01)
(Continued)

(52) U.S. Cl.
CPC ............. *C12M 47/04* (2013.01); *C12M 25/08* (2013.01); *C12M 33/00* (2013.01); *C12M 35/02* (2013.01); *C12M 47/02* (2013.01); *C12M 23/20* (2013.01); *C12M 41/36* (2013.01)

(58) Field of Classification Search
CPC .... C12M 23/20; C12M 24/08; C12M 35/02; C12M 47/02; C12M 47/0255; C12M 23/10; C12M 33/00
See application file for complete search history.

(56) References Cited

U.S. PATENT DOCUMENTS 6,001,617 A      12/1999  Raptis
2008/0057505 A1   3/2008  Lin et al.
(Continued)

FOREIGN PATENT DOCUMENTS

JP    10042857 A    *  2/1998
JP    2008-54511 A     3/2008
(Continued)

OTHER PUBLICATIONS

English language translation of JP10-042857 (Feb. 17, 1998), pp. 1-13.*
(Continued)

*Primary Examiner* — William H Beisner
(74) *Attorney, Agent, or Firm* — Baker Botts L.L.P.

(57) ABSTRACT

Disclosed is a cell culture vessel of the present invention, which is composed of a space enclosed by a housing that supports a medium and a cell attachment part, disposed on the bottom surface of the space, that attaches and supports the cells, the cell attachment part having a cell immobilizing mechanism that guides the cells in the space to the cell attachment part to immobilize there and a cell detachment mechanism that detaches the cells attached in the cell attachment part, the cell immobilizing mechanism having a step of applying a voltage to an electrode disposed in the cell attachment part to generate a heterogeneous electric field in the space, and the cell detachment mechanism having a step of applying a voltage to an electrode disposed in the cell attachment part to induce electrolyte in the space.

12 Claims, 17 Drawing Sheets

(51) Int. Cl.
*C12M 1/42* (2006.01)
*C12M 1/12* (2006.01)
*C12M 1/26* (2006.01)
*C12M 1/34* (2006.01)

(56) References Cited

U.S. PATENT DOCUMENTS

2008/0171372 A1 7/2008 Sokolov et al.
2009/0325256 A1 12/2009 Yasukawa et al.
2012/0264186 A1 10/2012 Koyama

FOREIGN PATENT DOCUMENTS

| JP | 2009-291097 A | 12/2009 |
| JP | 2012-254057 A | 12/2012 |
| JP | 2013-42682 A | 3/2013 |
| WO | 2008/018390 A1 | 2/2008 |
| WO | WO 2011/052717 A1 | 5/2011 |
| WO | 2012/169493 A1 | 12/2012 |

OTHER PUBLICATIONS

Extended European Search Report, mailed Jan. 20, 2015, which issued during the prosecution of European Patent Application No. 12796604.2, which corresponds to the present application.

Junya Suehiro et al., Quantitative estimation of biological cell concentration suspended in aqueous medium by using dielectrophoretic impedance measurement method, J. Phys. D: Appl. Phys. 32(1999) 2814-2820, Printed in UK.

Horoaki Shinohara et al., Real Time Observation of Dopamine Release from a Nerve Model Cell with the Microelectrode Detection System (Univ. of Toyama).

\* cited by examiner

CELL CULTURE DEVICE

TECHNICAL FIELD

The present invention relates to a cell culture vessel and a culture device. In particular, the present invention relates to a method for improving incubation efficiency.

BACKGROUND ART

Regenerative medicine has gotten a lot of attention as an innovative medical treatment, which enables basic remedy for damaged and/or defective cells, tissues, and organs. The regenerating tissue used for regenerative medicine, which is produced through the steps of collecting cells from the body of a patient or the other person; separating and purifying the collected cells in vitro, and growing and organizing the cells into tissue, is transplanted into the body of the patient. Tissue engineering, making advances yearly, has enabled the methods for forming one kind of cells into a sheet and for arranging several kinds of cells sterically to assemble an organ by artificial means to be developed.

To amplify therapeutic cells, in particular adherent cells in large quantities, an incubator large in area is useful. It is because adherent cells are amplified while expanding in the planar direction. On the other hand, it has a problem that as the area of an incubator becomes larger, its culture surface increasingly deforms; thereby, cells aggregate in a lower area, leading to deteriorated usage efficiency. As an effective technique for manipulating cells, electrophoresis has gotten attention. The systematic study and theoretical analysis of electrophoresis were set out by Pohl in 1970s (see Nonpatent Literature 1). Micro biological substances, such as bacteria and cells, have been already employed as a principal target to be manipulated since the initial study; accordingly, biotechnology is one of key applications of electrophoresis.

A dielectrophoretic force $F_{DEP}$ exerted on dielectric particles is given by the following equation 1 (see Nonpatent Literature 1). In the following paragraph, how to calculate is explained taking an example of dielectric particles being cells.

[Mathematical formula 1]

$$F_{DEP} = 2\pi a^3 \varepsilon_0 \varepsilon_m Re[K] \nabla E^2 \quad \text{(Formula 1)}$$

Where a is the radius of a cell approximated to a spherical shape, $\varepsilon_0$: electric permittivity in vacuum, $\varepsilon_m$: specific electric permittivity in medium, E: electric field intensity, and $\nabla$ is an operator representing a gradient. In this case, $\nabla E^2$, which is the gradient for the square of an electric field intensity ($E^2$), indicates how degree $E^2$ inclines at that point, namely, how suddenly the electric field spatially changes. K is called a Claudius-Mossotti number and is represented by an equation 2. Herein, assuming that $\varepsilon_b^*$ and $\varepsilon_m^*$ be complex dielectric constants for cells and a medium, respectively, and Re [K] be the real part of the Claudius-Mossotti number, Re [K]>0 represents positive electrophoresis and the cells migrate in the same direction as that of the electric field gradient, namely toward an electric field concentration part. Re [K]<0 represents negative electrophoresis and cells migrate in the direction apart from the electric field concentration part, namely toward a weak electric field part.

[Mathematical formula 2]

$$K = \frac{\varepsilon_b^* - \varepsilon_m^*}{\varepsilon_b^* + 2\varepsilon_m^*} \quad \text{(Formula 2)}$$

Formula 3 generally represents complex dielectric constant $\varepsilon_r^*$.

[Mathematical formula 3]

$$\varepsilon_r^* = \varepsilon_r - j\frac{\sigma}{\omega\varepsilon_0} \quad \text{(Formula 3)}$$

Where, $\varepsilon_r$ is the specific electric permittivity for a cell or medium, $\sigma$ is the electric conductivity of a cell or medium, and $\omega$ is the angular frequency of an applied electric field. As known from Formulae 1, 2, and 3, a dielectrophoretic force depends on the radius of a cell, the real part of a Claudius-Mossotti number, and an electric field intensity. Moreover, it is known that the real part of the Claudius-Mossotti number varies depending on the complex electric permittivity and electric field frequency of a cell and medium.

The DEPIM method, combining dielectrophoresis and impedance measurement, has been proposed as a method for measuring microbial counts using dielectrophoresis. The DEPIM method is characterized in that these parameters are appropriately selected and a positive dielectrophoretic force exerted on microorganisms is sufficiently increased to collect the microorganisms into an electrode gap, making electrical measurement to determine a microbial count in the sample solution (see Nonpatent Literature 2).

In addition, a culture device, which eliminates unnecessary cells from a cell suspension using negative dielectrophoresis to culture necessary cells at high concentrations, is disclosed (see Patent Literature 1 and Patent Literature 3).

Moreover, a method and apparatus, for collecting cells efficiently in a target area without losing the activity of functional cells using positive dielectrophoresis, is disclosed (see Patent Literature 2).

CITATION LIST

Patent Literature

Patent Literature 1: Japanese Unexamined Patent Application Publication No. 2009-291097
Patent Literature 2: Japanese Unexamined Patent Application Publication No. 2008-54511
Patent Literature 3: US Patent Application Publication No. 2008/0057505, Specification

Nonpatent Literature

Nonpatent Literature 1: H. Pohl: Dielectrophoresis, Cambridge University Press, Cambridge (1978)
Nonpatent Literature 2: J. Suchiro, R. Yatsunami, R. Hamada, M. Hara, J. Phys. D: Appl. Phys. 32 (1999) 2814-2820

SUMMARY OF INVENTION

Technical Problem

However, it is difficult to manipulate cells and microorganisms directly in an ion-rich culture solution (namely, high electric conductivity) using dielectrophoresis described in BACKGROUND. For this reason, generally, the target cells are moved in an ion-poor buffer solution, manipulated, and then returned back in the original culture solution. As a result, a cell manipulation process is complicated, causing a problem of increased stress on the cells due to a change in culture environment. In addition, this method has another problem that generally, an enzyme is used to detach the cells grown during surface culture from the surface of culture medium, increasing load on the cells.

An object of the present invention is to simplify the cell manipulation process to reduce the stress on the cells, as well as the load on the grown cells exerted when detached from the surface of the culture medium in order to solve these problems. This makes possible to improve culture efficiency of a cell culture vessel and determine cell distribution and growth via electric signals.

Solution to Problem

To address the aforementioned problems, the key characteristics of the cell culture vessel of the present invention are as described below.

A cell culture vessel for supporting and culturing cells is composed of a space enclosed by a housing for supporting a medium and a cell attachment part disposed on the bottom surface of the space for attaching and supporting the cells therein. The cell attachment part has a cell immobilizing mechanism for guiding the cells to the cell attachment part from the cell space and immobilizing them therein, and a cell detachment mechanism for detaching the cells attached in the cell attachment part. The cell immobilizing mechanism includes a step of applying voltage in an electrode to generate an inhomogeneous electric field in the space, and the cell detachment mechanism includes a step of applying voltage in an electrode disposed in the cell attachment part to induce electrolysis in the space.

A cell culture device of the present invention is mainly characterized as described below. The cell culture device equipped with the cell culture vessel for supporting and culturing the cells therein is composed of a feeding/discharging part for feeding/discharging the medium into/from the cell culture vessel, and a power source for applying voltage to an electrode disposed in the cell culture vessel. A cell culture vessel is composed of a space enclosed by a housing for supporting a medium and a cell attachment part disposed on the bottom surface of the space for attaching and supporting the cells therein. The cell attachment part has a cell immobilizing mechanism for guiding the cells into the cell attachment part from the cell space and immobilizing them therein, and a cell detachment mechanism for detaching the cells attached in the cell attachment part. The cell immobilizing mechanism includes a step of applying voltage in an electrode to generate an inhomogeneous electric field in the space, and the cell detachment mechanism includes a step of applying voltage in an electrode disposed in the cell attachment part to induce electrolysis in the space.

It has been known that in the ion-rich environment with the electric conductivity of the medium equal to or less than 1000 mS/m, dielectrophoresis becomes negative always at the frequency equal to or less than $10^9$ Hz. Taking advantage of cell migration in the direction apart from the electric field concentration, namely toward the weak electric field by negative electrophoresis, the present invention enables the cells to be immobilized in a desired location.

The cells may be detached from the surface of the culture medium by applying a direct current (DC) field; thereby, the need for the use of any enzyme (e.g., trypsin) in cell detachment, as with traditional apparatuses, is eliminated.

Advantageous Effects of Invention

The present invention enables the culture efficiency of the cell culture vessel to be improved and the cell distribution and growth to be determined via electric signals.

DESCRIPTION OF EMBODIMENTS

Figure 1:
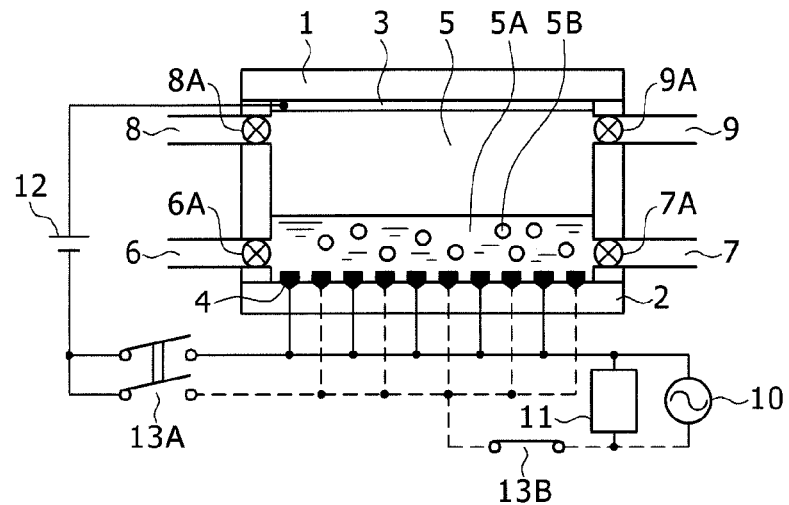
FIG. 1 is a diagram showing one configuration of a cell culture vessel of the present invention.

Hereinafter, by reference to the accompanying drawings, the embodiments of the present invention will be explained. It should be noted that the same signs are assigned to the same components in the drawings and the explanation of these components are omitted.

Hereinafter, by reference to the accompanying drawings, the embodiments will be explained.

First Embodiment

One example of the cell culture vessel of the present invention will be explained by reference to FIG. 1.

In FIG. 1, 1 is the ceiling substrate of the cell culture vessel, 3 is an upper electrodes including an electrode couple, which is disposed on the ceiling substrate 1. 2 is a bottom substrate of the cell culture vessel, 4 are lower electrodes for immobilizing the cells, which is disposed on the bottom substrate. 5 is an internal space of a cell culture vessel, and 5A is a medium containing cells 5B. 6 is a medium inlet, at which a valve 6A is disposed, 7 is a medium outlet, at which a valve 7A is disposed, 8 is a mixed gas inlet, at which a valve 8A is disposed and 9 is a mixed gas outlet, at which a valve 9A is disposed. 10 is an AC power source and 11 is an impedance measuring apparatus for measuring impedance between the electrode couple. 12 is a DC power source, 13A is a switch for conducting electricity from the upper electrode 3 to the lower electrode 4 through the DC power source 12, and 13B is a switch for conducting electricity from the AC power source 10 to the lower electrode 4.

Figure 2:
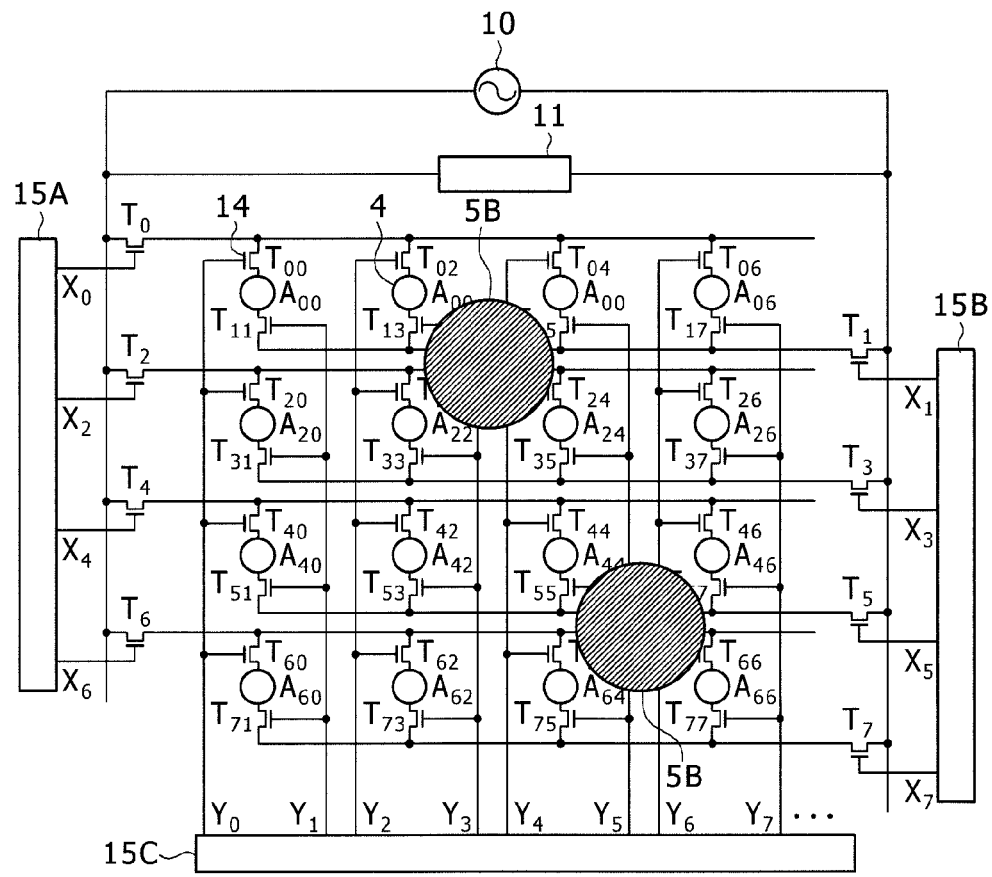
FIG. 2 is a diagram showing one configuration of an electrode disposed in a cell immobilizing mechanism of the present invention.

FIG. 2 is a plan view showing one configuration of the electrodes disposed in the cell immobilizing mechanism. 4 is a thin film electrode disposed on the bottom surface and 14 is an on/off switch for supplying or interrupting current to/from the power source 10. 15A, 15B, and 15C are driving circuits for controlling the switch 14.

The aforementioned the ceiling substrate 1 and the bottom substrate 2 may be formed using any of insulating materials, as their base material, such as glass, silicone, quartz plastics, polymers. Preferably, the ceiling substrate 1 and the bottom substrate 2 are formed using, as their material, any of materials with light transmittance to the degree that the cells are enabled to be observed under an optical microscope, and more preferably, for the surface of the bottom substrate 2, a material is used, which may be modified through cleaning and preprocessing processes before the cells are attached thereon.

Figure 3:
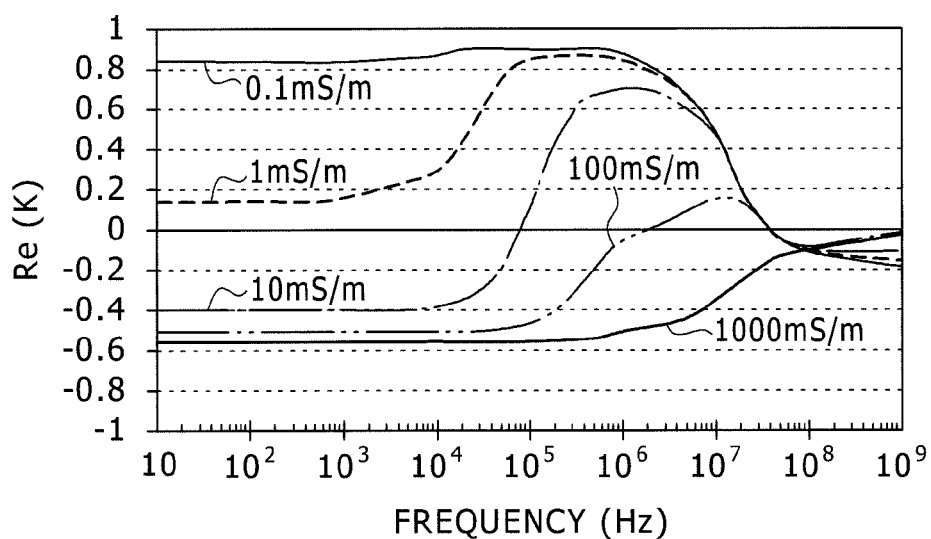
FIG. 3 is a diagram illustrating the relationship between the frequency of an alternate current (AC) field and the real part Re [K] of a Claudius-Mossotti number.

Generally, an ion-rich, highly-conducting medium (1000 mS/m) is used for cell culture, in particular for animal cell culture. FIG. 3 is a diagram showing the relationship between the frequency of a DC electric field and the real part Re [K] of a Claudius-Mossotti number. As known from the figure, when the electric conductivity of the medium is equal to or higher than 1000 mS/m, dielectrophoresis is negative dielectrophoresis (negative DEP) in all cases at the frequency equal to or lower than $10^9$ Hz. Specifically, the cells migrate in the direction away from the center of the electric field, namely toward the weak electric field. It should be noted that preferably, the applied frequency is equal to or lower than $10^7$ Hz because the dielectrophoretic force is proportional to the amplitude of Re [K].

Figure 4:
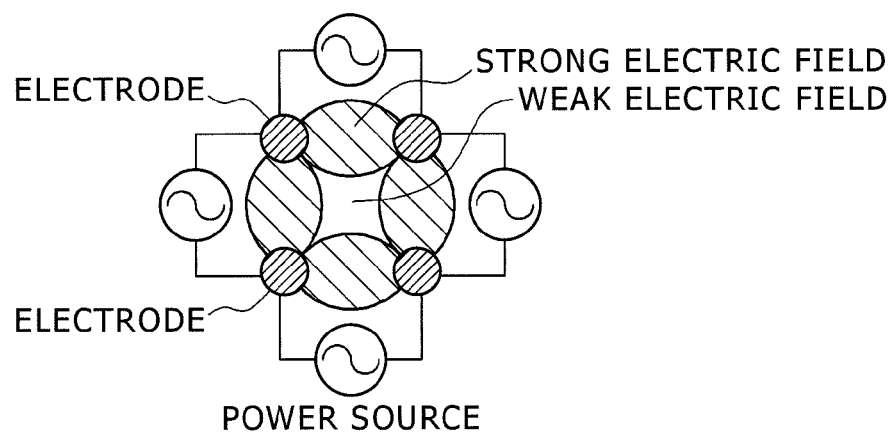
FIG. 4 is a diagram illustrating the use of circular electrodes as cell immobilizing electrodes.

As shown in FIG. 4, at the center of the four electrodes disposed in the cell immobilizing mechanism according to the first embodiment, a weak electric field is formed. This enables the cells in the highly-conducting medium to migrate into this weak electric field and be immobilized there. Moreover, individually controlling these four electrodes allows for control of cell distribution. It goes without saying that circular electrodes have been described in regard to the first embodiment, but rectangular or polygonal electrodes may be used.

Figure 5:
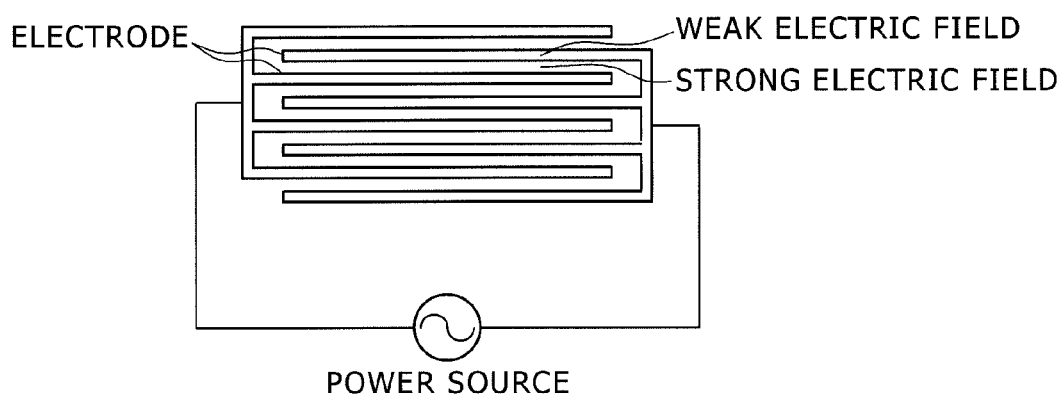
FIG. 5 is a diagram illustrating the use of comb-shaped electrodes as the cell immobilizing electrodes.
Figure 6:
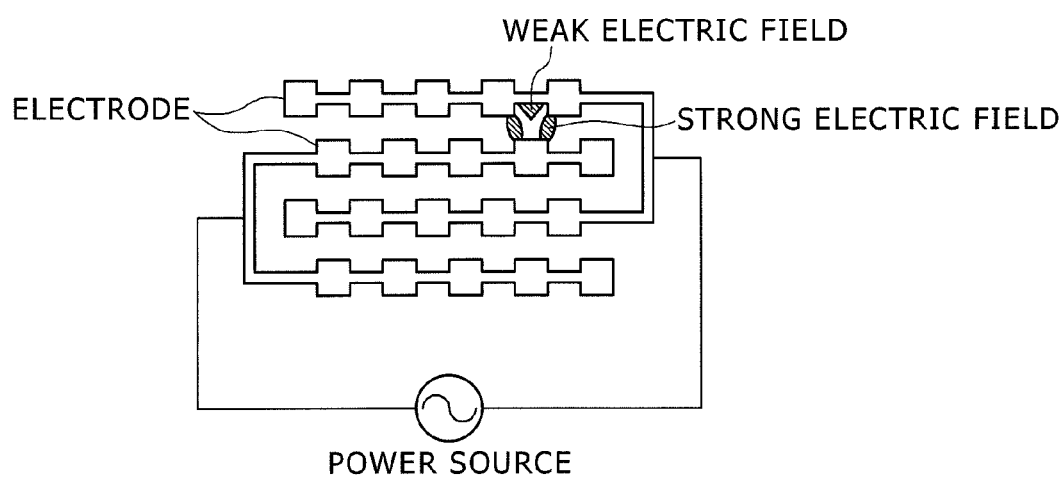
FIG. 6 is a diagram illustrating the use of castle-wall electrodes as the cell immobilizing electrodes.

The present invention is not limited to the electrodes according to the aforementioned first embodiment but may be the electrodes formed into the shape capable of generating the weak electric field shown in FIG. 5 and FIG. 6; it is because this type of electrodes enable the cells in the highly-conducting medium to migrate into the weak electric field and be immobilized there through a negative dielectrophoretic force.

In the case of the cells culture on the surface of the medium, it is desired that to grow the cells, a layer for facilitating cell attachment capacity, for example a polymeric membrane, is coated between the bottom surface of the incubator between the electrodes, as well as the surfaces of the electrodes.

Hereinafter, by reference to FIGS. 7, 8, 9, and 10, the flow of a process involving the steps of seeding cells homogenously, culturing the cells for growth, and detaching the cells is explained.

Figure 7:
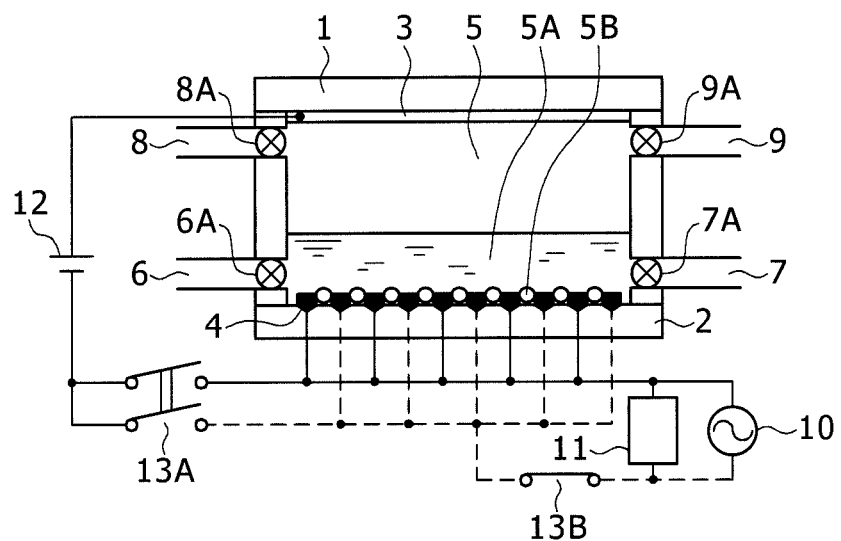
FIG. 7 is a diagram illustrating how to immobilize the cells by the cell immobilizing electrodes of the present invention.

As shown in FIG. 7, cells 5B seeded in five mediums 5A in the cell culture vessel migrate into many weak electric fields of the lower electrode 4 and are immobilized there separately. Accordingly, it is possible to suppress the influence of the deformed bottom surface of the cell culture vessel, external vibrations during cell seeding, and medium vibration, achieving homogenous cell seeding over the whole surface of the cell culture vessel. Homogenous cell seeding improves the use efficiency of the cell culture vessel, increasing cell culture efficiency. Moreover, measuring changes in impedance in the gap between the lower electrodes 4 makes it possible to estimate the distribution of cells immobilized in the weak electric fields. Using this advantage, the cell distribution may be easily estimated using electric signals rather than an optical microscope.

Figure 8:
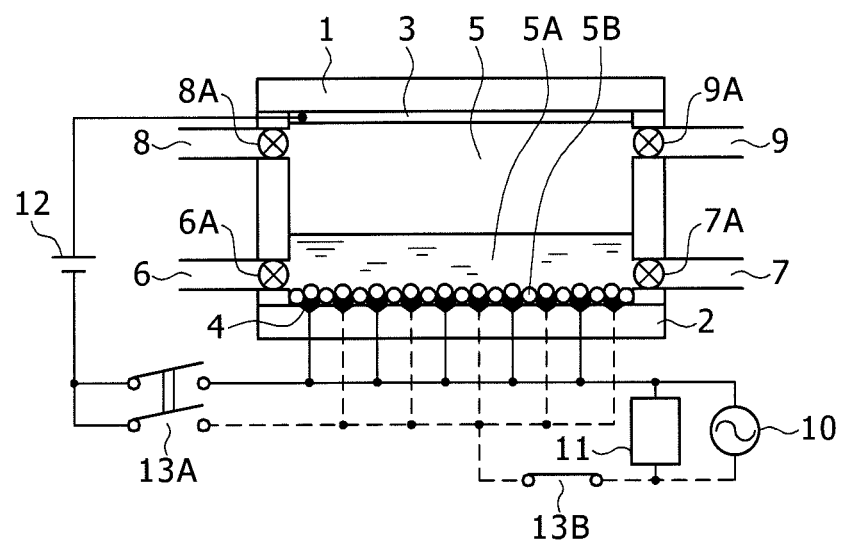
FIG. 8 is a diagram illustrating how to grow the cells in the cell culture vessel of the present invention.

During the step of culturing the cells (for example, animal cells) for growth, the cells are attached to the culture surface at 37° C. for growth. During the step of exchanging a mixed gas for culture (composed of air, 5% $Co_2$, and 100% water), as shown in FIG. 8, the gas is introduced into the cell culture vessel from a mixed-gas inlet 8 thereof, and waste gas produced by culture is discharged from a mixed-gas outlet 9. During the step of exchanging the medium, a new medium is introduced from a medium inlet 6 and waste medium is discharged from a medium outlet 7. Since the culture surface is disposed directly above the lower electrodes 4, measuring changes in impedance in the gap between the lower electrodes 4 allows for estimation of cell growth progress. This enables real-time measurement of the cell growth progress through the electric signals with no need for observation of the progress under an optical microscope.

Figure 9:
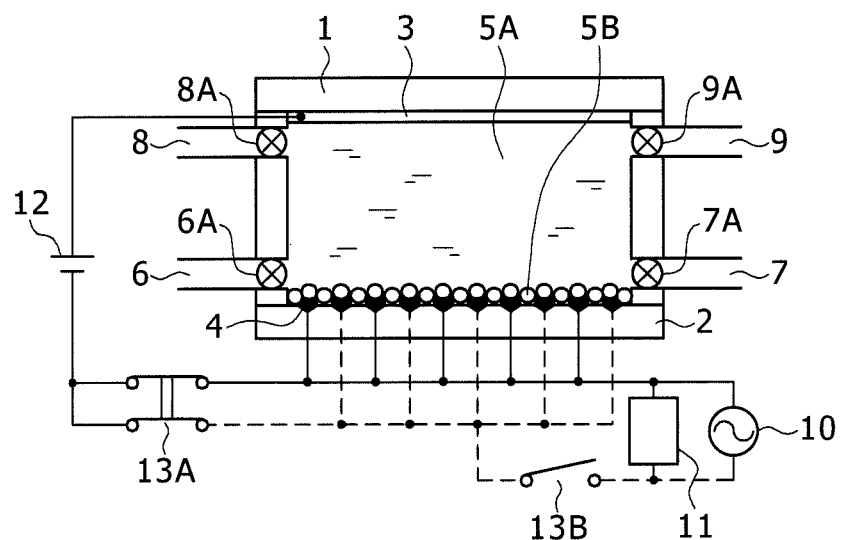
FIG. 9 is a view showing the state of the cell culture vessel before the cells are detached by the electrodes disposed in the cell detachment mechanism of the present invention.
Figure 10:
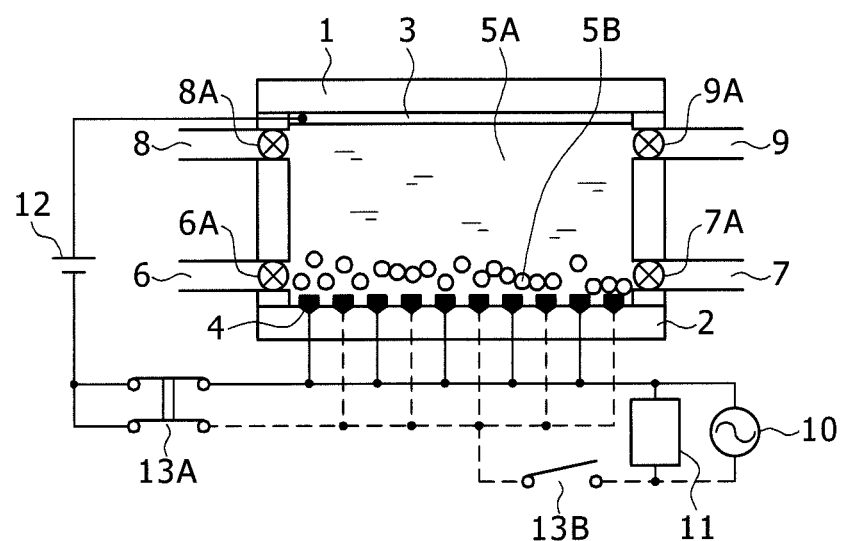
FIG. 10 is a view the state of the cell culture vessel after the cells are detached by the electrodes disposed in the cell detachment mechanism of the present invention.

To detach the grown cells from the culture surface, as shown in FIG. 9, first, the cell culture vessel is filled with the medium 5A. Then, the switch 13B is turned OFF and the switch 13A is turned ON. This operation applies the DC electric field is applied between the lower electrode 4 and the upper electrode from the DC power source 12. Applying an appropriate DC voltage enables the cells to be detached from the culture surface, as shown in FIG. 10, by the effect of electrolysis occurring on the surface of the lower electrode. In this case, the cells may be detached with no need for using the enzyme (for example, trypsin) as with conventional techniques. Accordingly, the cost of an enzyme may be saved.

The cells contained in the medium precipitate, when left as it is, spontaneously down toward the bottom of the cell culture vessel under its own weight. However, it takes long time, about several hours, for the cells to reach the bottom of the incubator and initiate their growth, especially for light cells; thereby they are likely to die before they initiate their growth. To solve this problem, it is required that an appropriate voltage is applied to facilitate cell immobilization. However, even though the voltage is applied, the precipitated cells are eccentrically deposited; thereby it is not expected that the cells grow homogeneously over a wide range.

According to the first embodiment of the present invention, it is expected that the death of the cells may be avoided.

Moreover, according to the first embodiment of the present invention, the cell culture vessel of the present invention enables the cells to be incubated more efficiently, the distribution and growth progress of the cells to be estimated, and the cells to be detached from the culture surface through electrophoresis. In other words, the cell culture vessel according to the first embodiment of the present invention has advantages of improving cell culture efficiency and reducing the running cost of the apparatus using the cell culture vessel.

Second Embodiment

With regard to the second embodiment of the present invention, explained is a method for estimating the distribution and growth progress of the cells by measuring the impedance between the lower electrodes of the present invention.

Hereinafter, assuming that the impedance between the lower electrodes be Z, capacitance be C, reactance be x, resistance be r, and resistor be R, the aforementioned method is explained using formulas 4 to 8 by reference to FIG. 11.

[Mathematical formula 4]

$$Z = \frac{R - j\omega R^2 C}{1 + \omega^2 R^2 C^2} \quad \text{(Formula 4)}$$

[Mathematical formula 5]

$$r = \frac{R}{1 + \omega^2 R^2 C^2} \quad \text{(Formula 5)}$$

[Mathematical formula 6]

$$x = \frac{-j\omega R^2 C}{1 + \omega^2 R^2 C^2} \quad \text{(Formula 6)}$$

[Mathematical formula 7]

$$R = r + \frac{x^2}{r} \quad \text{(Formula 7)}$$

[Mathematical formula 8]

$$C = \frac{x}{\omega(r^2 + x^2)} \quad \text{(Formula 8)}$$

The formula 4 represents a synthetic impedance Z in a CR parallel equivalent circuit, the formula 5 represents a resistance r in the CR parallel equivalent circuit, the formula 6 represents a reactance x in the CR parallel equivalent circuit, the formula 7 represents a resistor R in the CR parallel equivalent circuit, and the formula 8 represents capacitance C in the parallel equivalent circuit.

Figure 11:
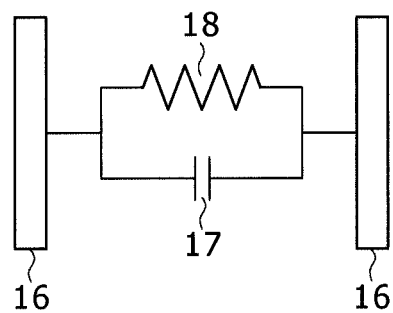
FIG. 11 is a view illustrating an equivalent circuit for the cells in the gap formed between the electrodes.

FIG. 11 shows the electric state between the lower electrodes 16 of the cell culture vessel by means of the equivalent circuit. There exists the medium containing the cells between the electrodes 16. The capacitance (C) 17 configured using the medium as an inter-electrode dielectric and the electric resistor (R) 18 connect in parallel between the electrodes 16 before the cells migrate into the gap between the electrodes. Specifically, the count of the cells, which are locally immobilized may be estimated based on the degree, to which the impedance between the lower electrodes of the cell culture vessel. Moreover, when the locally immobilized cells divide and grow, the impedance increases; this makes it possible to estimate the cell growth progress. Accordingly, electric signals may be used to assess the cell growth progress easily and rapidly with no observation under an optical microscope.

Third Embodiment

With respect to the third embodiment of the present invention, the gap distance between the electrodes of the cell immobilizing mechanism, applied voltage, and applied frequency are explained.

An electric field intensity E between the electrodes of the cell immobilizing mechanism may be represented by the formula 9.

[Mathematical formula 9]

$$E = \frac{V}{d} \quad \text{(Formula 9)}$$

Where, E is the electric field intensity, V is the applied voltage, and d is the gap distance. Water, which is a principal component of the medium for the cell culture, undergoes electrolysis theoretically at 1.23 V; thereby, the applied voltage V need to be set to 1.23 V and preferably, it is equal to and higher than 1 V. However, a lower applied voltage has a disadvantage that it induces only a weak dielectrophoretic force, taking long time for cell growth; accordingly, the lower limit of the applied voltage is preferably approx. 20 mV from the practical view. Moreover, when the cells are manipulated using the thin film electrodes, the electric field intensity E need to be equal to or higher than $1 \times 10^4$ V/m; thereby gap distance d between electrodes becomes equal to or lower than 123 µm. Furthermore, in the case of the cells, the average diameter of them is 10 µm; accordingly, the gap distance between the electrodes is preferably 20 to 30 µm. The formula 10 represents the amplitude of the impedance between the aforementioned electrodes.

[Mathematical formula 10]

$$|Z| = \frac{d}{s} \frac{1}{\sqrt{\sigma_m^2 + (2\pi f \varepsilon_0 \varepsilon_m)^2}} \quad \text{(Formula 10)}$$

Where S is the facing surface areas of the electrodes. As known from the formula 10, with d between the electrode gaps being constant, the larger the applied frequency f, the smaller the impedance. Specifically, applying high frequency decreases the resistance between the electrodes, causing a larger current to flow. This elevates the medium temperature, causing the environment appropriate for cell culture to be deteriorated or a current control system to be complicated. In addition, considering the technique for achieving a high frequency apparatus, to gain a practical dielectrophoretic force, the applied frequency is preferably equal to or lower than 10 MHz. However, with a lower applied frequency, electrolysis of water occurs readily; accordingly, the lower limit is preferably approx. 100 Hz.

Fourth Embodiment

With respect to the fourth embodiment, another cell culture vessel of the present invention is explained by reference to FIGS. 12 and 13.

Figure 12:
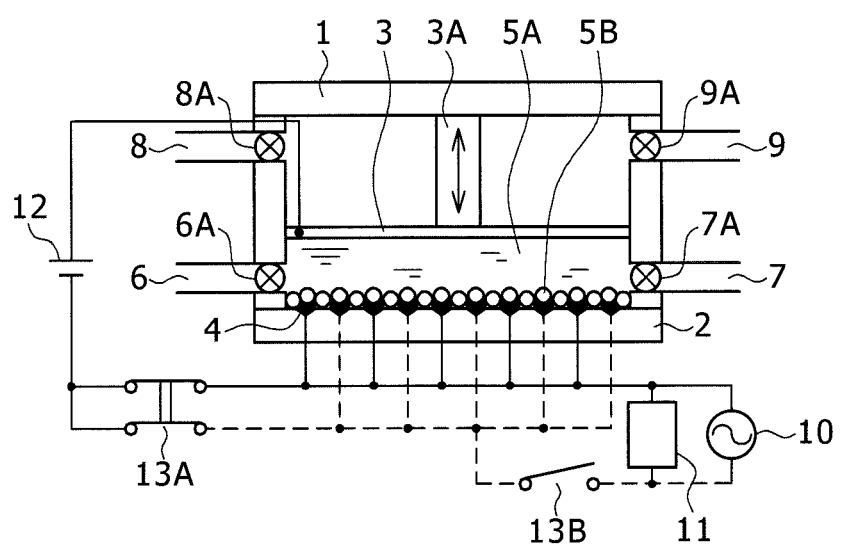
FIG. 12 is a diagram showing another configuration of the electrodes disposed in the cell detachment mechanism of the present invention.
Figure 13:
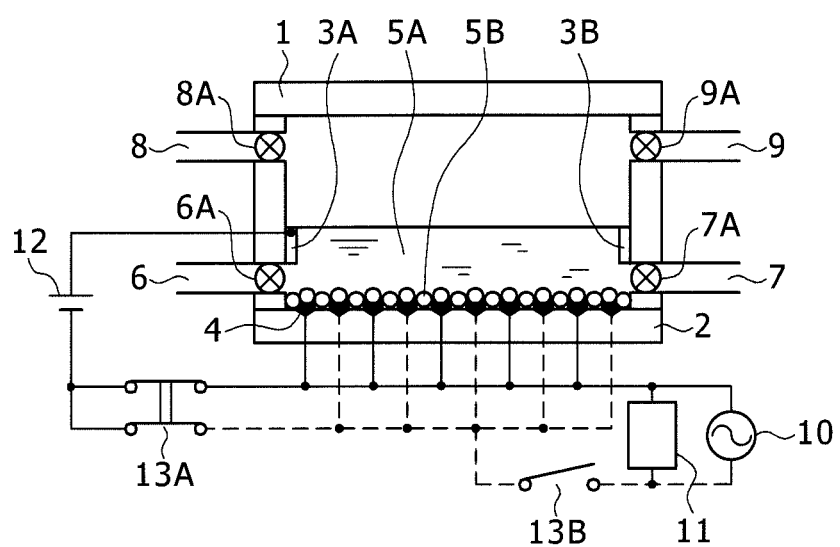
FIG. 13 is a diagram showing the other configuration of the electrodes disposed in the cell detachment mechanism of the present invention.

In the fourth embodiment, an expansion mechanism 3A shown in FIG. 12 and a side electrode 3B shown in FIG. 13 are the same as those in the first embodiment. Hereinafter, the same signs are assigned to the same parts as those described with respect to the first embodiment to omit duplicated explanation and only different parts will be explained.

In the cell culture vessel configured as shown in FIG. 12, to detach the cultured and grown cell, the upper electrode 3 is caused to come into contact with the top surface of the medium 5A by means of an expansion mechanism, and turns the switch 13B OFF and the switch 13A ON. This operation applies a DC electric field between the lower electrode 4 and the upper electrode 3 from the power source 12. Applying an appropriate voltage enables the cells to be detached from the culture surface through the effect of electrolysis occurring on the surface of the lower electrode.

In the cell culture vessel shown in FIG. 13, the electrodes of the detachment mechanism are disposed on the side surface of the cell culture vessel. Moreover, the switch 13B is turned OFF and the switch 13A is turned ON. This operation applies a DC electric field between the lower electrode 4 and the upper electrode 3 from the power source 12. Applying an appropriate voltage enables the cells to be detached from the culture surface through the effect of electrolysis occurring on the surface of the lower electrode.

Example 1

Figure 14:
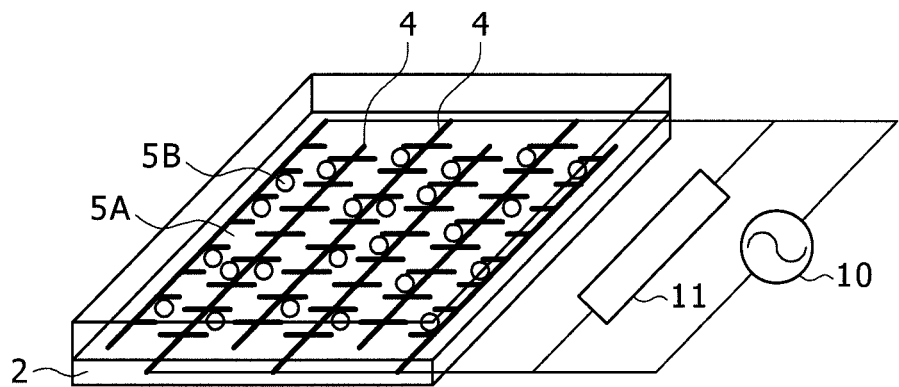
FIG. 14 is a view showing the state of the cell culture vessel after the cells have been seeded according to an example 1.
Figure 15:
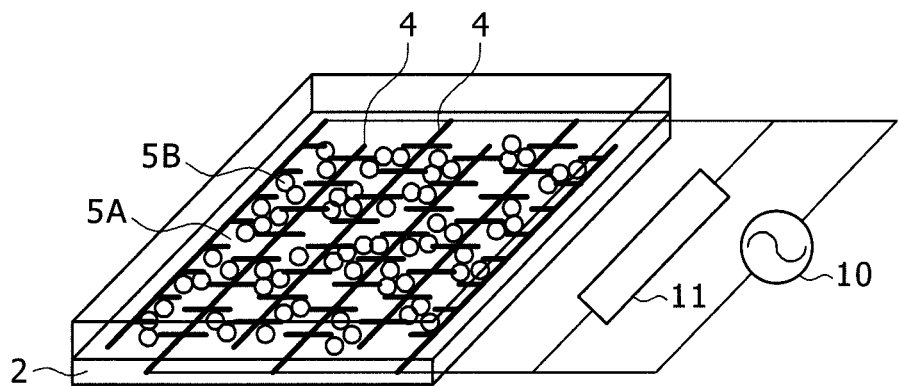
FIG. 15 is a view showing the state of the cell culture vessel after the cells have been grown according to the example 1.

In the example 1, a castle-wall electrodes are used for cell immobilization, cell count measurement, and cell growth progress measurement. FIG. 14 shows the state of the medium after cell seeding and FIG. 15 shows the state of the medium after cell growth. In the example 1, 3T3 cells (cultivated strain of the fibroblast cells derived from mouse skin), and the DMEM medium with calf serum and an antibiotic substance added are used. Note that the average diameter of 3T3 cells is 10 µm and the electric conductivity of the medium is 1200 mS/m.

Figure 16:
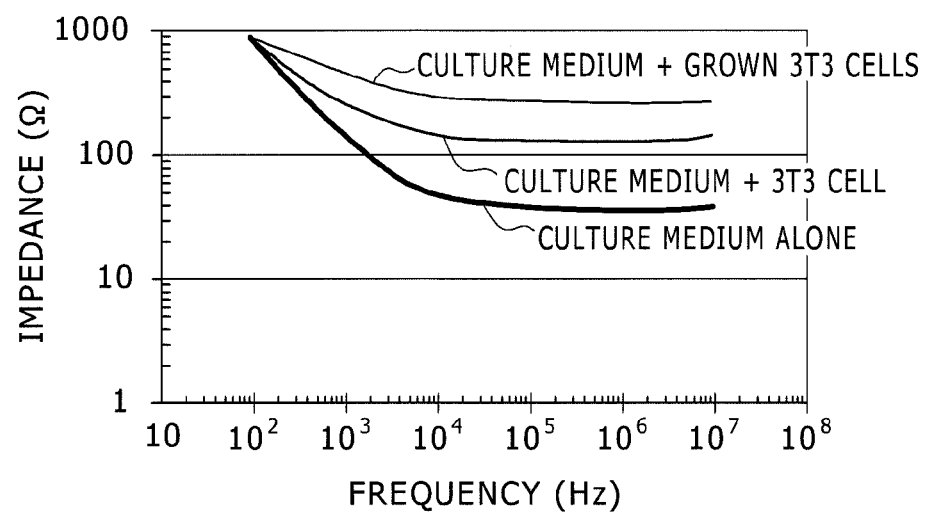
FIG. 16 is a view exemplifying the influence of an applied frequency on impedance between the electrodes of the present invention.
Figure 17:
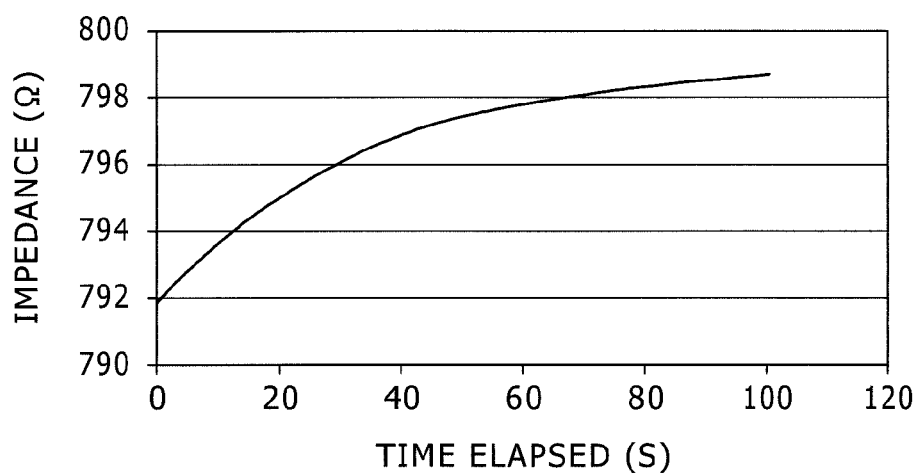
FIG. 17 is a view exemplifying a time-course change in impedance between the electrodes of the present invention.

FIG. 16 shows the influence of the applied voltage of 0.1 V on changes in impedance between the electrodes with the gap distance between the electrodes of 20 m. As known from FIG. 16, the impedance of the medium containing the 3T3 cells is higher than that of the medium alone. It is because the 3T3 cells have been immobilized in the weak electric field by the negative dielectrophoretic force. FIG. 17 shows a time-course change in impedance between the electrodes at the applied voltage of 0.1 V and the applied frequency of 1 KHz. The impedance between the electrodes clearly increased over time. This suggests that the cells in the medium are rapidly immobilized in the weak electric field between the electrodes. Moreover, comparison of this change in impedance with the result of microscopic observation gives the impedance count for each cell; accordingly, the count of the immobilized cells between the electrodes may be found based on the change in impedance.

With respect to the example 1, the result of the use of the 3T3 cells and the DMEM medium have been explained; however, the use of the cells derived from any other animal of comparable size and another medium with electric conductivity equivalent to that of the DMEM medium may give the same result.

As known from FIG. 16, after the cells are cultured for 24 hours at 37° C. while the mixed gas of air, 5% $CO_2$, and 100% water is being flown into the cell culture vessel the impedance between the electrodes further increases. This increase in impedance between the electrodes may be associated with the increased count of the cells after cell growth. Taking advantage of this phenomenon, the cell growth progress may be easily determined using the electric signals.

Example 2

With respect to the example 2, the result of an experiment, in which the cultured cells are detached from the medium surface using the detachment mechanism of the present invention. Since the experimental conditions are the same as those of the example 1, the explanation of them is omitted. After 24-hour culture, 0.5 V of voltage was applied between the upper electrode 3 and lower electrode 4 of the cell culture vessel from the DC power source 12. Two hours after applying the voltage, it was observed that the cells were gradually detached away from the medium surface. To facilitate this detachment step, the applied voltage may be increased; however, it is concerned about the possibility of damage to the cells due to strong electrolysis. Taking advantage of this phenomenon, the cells may be detached with no need for an enzyme for detachment as with conventional techniques, for example trypsin, reducing the running cost.

On the other hand, no technique method for concentrating the cells using dielectrophoresis has been reported.

With respect to the example 3 and its succeeding examples, an apparatus for concentrating the cells in the medium efficiently with less load on the cells using negative dielectrophoresis is explained.

Example 3

One configuration of the cell concentrating apparatus according to the example 3 of the present invention is explained by reference to FIG. 18.

Figure 18:
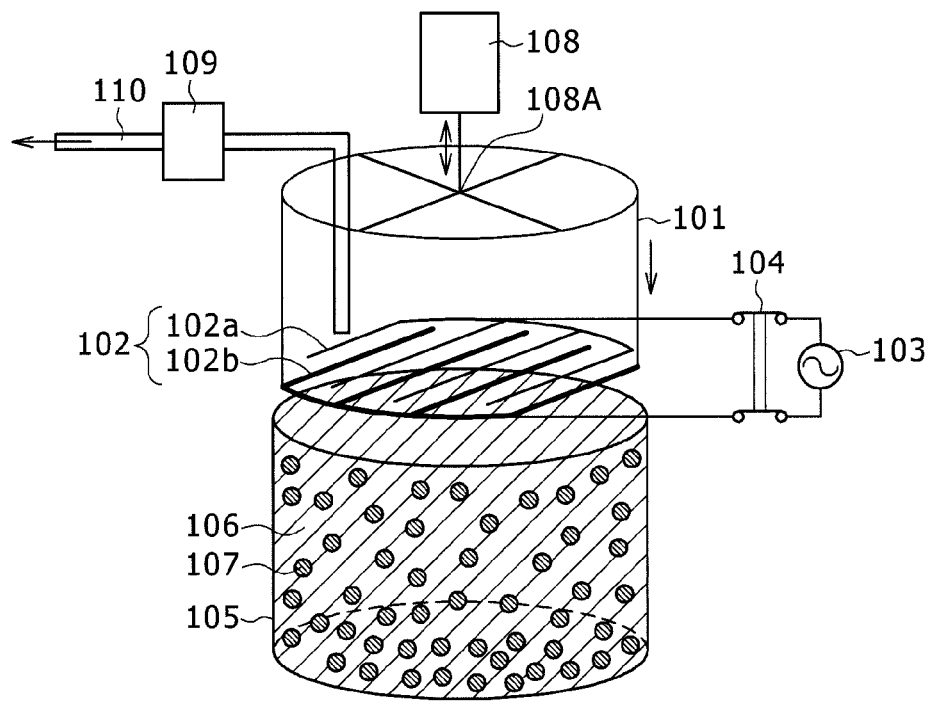
FIG. 18 is a view showing a cell concentration apparatus according to an example 3 of the present invention.

In FIG. 18, 101 is a piston-type incubator, 102 are concentrating electrodes containing electrode couples 102a and 102b disposed on the bottom surface of the piston-type incubator 101. 103 is an AC power source, 104 is a switch between the concentrating electrode 102 and the AC power source 103. 105 is a cell suspension vessel and 106 is the medium containing cells 107. 108 is a driving mechanism equipped with a support mechanism 108A. 109 is a discharge mechanism equipped with a discharge tube 110.

The concentrating electrode 102 disposed on the bottom surface of the piston-type incubator 101 may be formed directly of, for example metal wire, or may be formed by evaporating or fixing a metal material on a solid insulating substrate made of any of materials such as glass, silicone, quartz, plastics, and polymers and then forming a through hole between the electrodes. Moreover, it is desired that any of materials capable of suppressing the chemical reaction with the medium and the influence on the cells is used for the aforementioned electrodes and the support member. The allowable materials for the electrodes include platinum, gold, chromium, palladium, silver, aluminum, tungsten, and ITO, or any combination of them. It goes without saying that the cross-sectional shape of the concentering electrode is preferably circular but may be other shapes such as rectangle and polygon.

Figure 19:
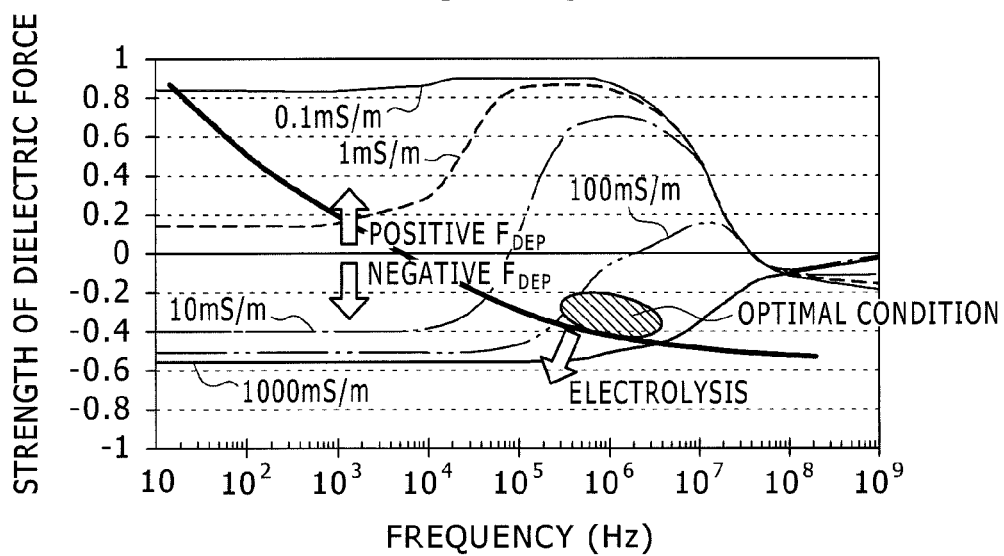
FIG. 19 is a view illustrating the relationship between the frequency of an AC electric field and the real part RE [K] of a Claudius-Mossotti number.

Generally, ion-rich media with high conductivity (1000 mS/m or higher) is used for culturing the cells, especially animal cells. FIG. 19 is a view showing the relationship between the frequency of the AC electric field and real part Re [K] of the Claudius-Mossotti number. In this figure, the results of dielectrophoresis are shown for each of media with electric conductivity of 0.1, 1, 10, 100, and 1000 mS/m. In the figure, the areas, where the dielectrophoretic force $F_{DEP}$ is positive and negative, are also shown. As known from this figure, with the media with electric conductivity equal to or higher than 1000 mS/m, dielectrophoresis becomes negative at the frequency equal to or lower than $10^9$ Hz in all cases. Specifically, the cells migrate in the direction away from the center of the electric field, namely toward the weak electric field. Note that since the dielectrophoretic force is proportional to the amplitude of Re [K], the applied frequency is preferably equal to or lower than $10^7$ Hz.

Figure 20:
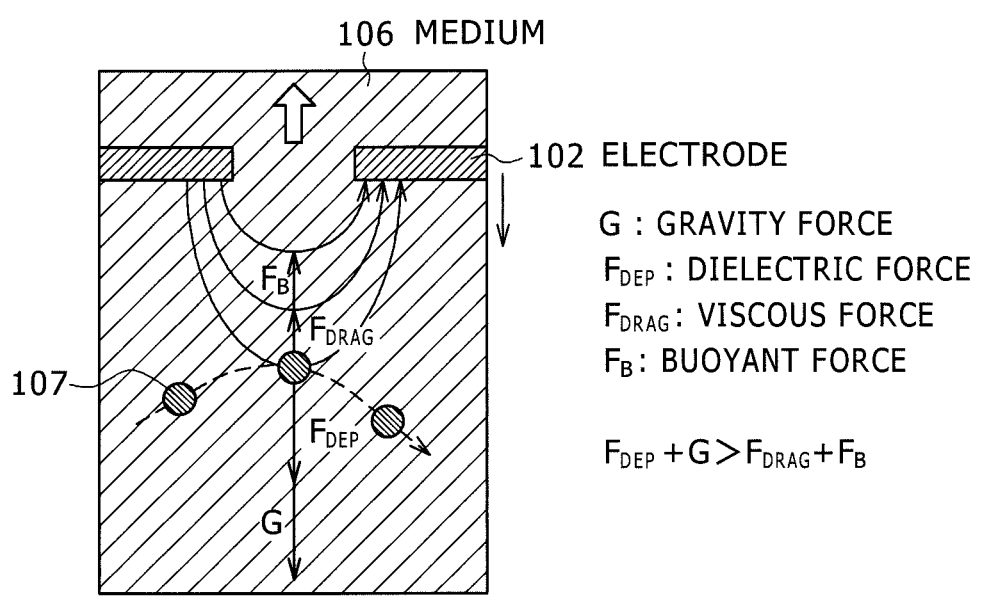
FIG. 20 is a view illustrating the principle of concentration of the cell by dielectrophoresis of the present invention.

By reference to FIG. 20, the principle of cell concentration will be explained. A gravity force G, buoyant force $F_B$, and viscous force $F_{DRAG}$ are exerted on the cells 107 seeded on the medium 106. In this case, when the concentrating electrode 102, to which the AC voltage is applied, approaches the cells 107, the dielectrophoretic force $F_{DEP}$ is further exerted thereon. When the concentrating electrode 102 is inserted down into the cell suspension vessel 105 vertically from the top side, the cells 107 contained in the medium move toward the bottom of the cell suspension vessel 105 together with the concentrating electrode 102, provided that the condition $F_{DEP}+G>F_B$ is met. At the same time, the medium passes through the gap between the concentrating electrodes 102 to the piston-type incubator 101, in which the medium is discharged. Thus, cell concentration may be achieved.

With respect to the example 3, the technique for inserting the concentrating electrode 102 down into the cell suspension vessel 105 vertically from the top side has been described; however, it goes without saying that the concentrating electrode 102 may be inserted from the bottom side or the lateral side. Insertion of the concentrating electrode 102 into the cell suspension vessel 105 from the top side is preferable because it improves cell concentration efficiency by exerting the gravity force G and the dielectrophoretic force from their individual directions.

Figure 21A:
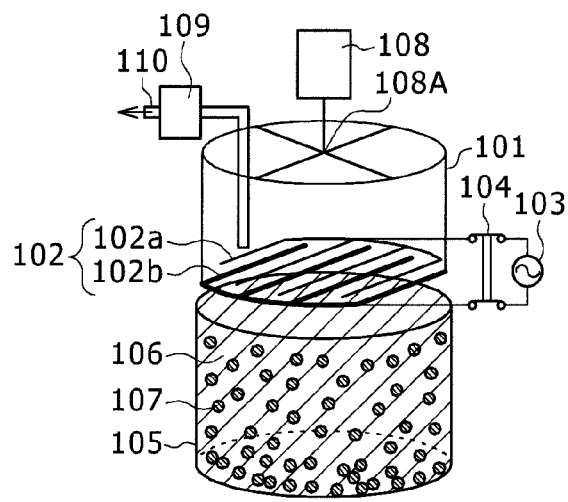
FIG. 21A is a view illustrating a flow A of cell concentration by the cell concentration apparatus according to the example 3 of the present invention.
Figure 21B:
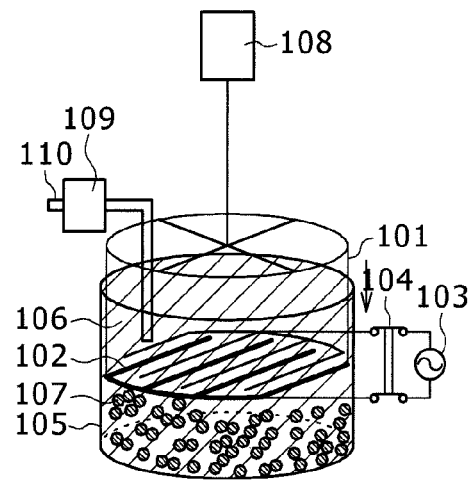
FIG. 21B is a view illustrating a flow B of cell concentration by the cell concentration apparatus according to the example 3 of the present invention.
Figure 21C:
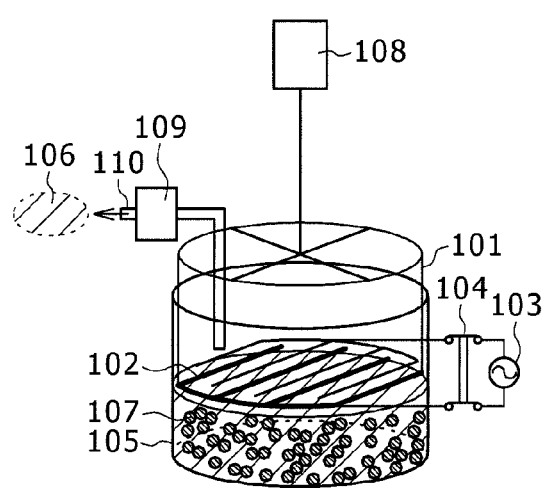
FIG. 21C is a view illustrating a flow C of cell concentration by the cell concentration apparatus according to the example 3 of the present invention.
Figure 21D:
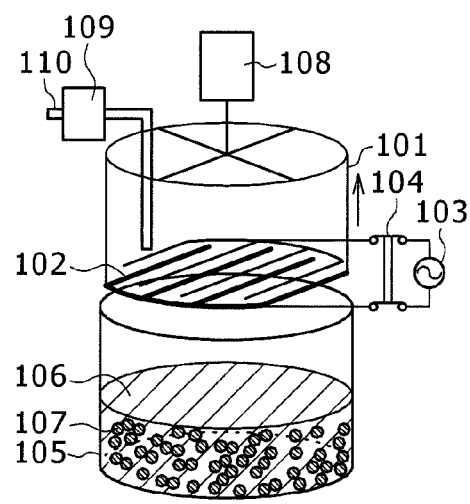
FIG. 21D is a view illustrating a flow D of cell concentration by the cell concentration apparatus according to the example 3 of the present invention.

By reference to FIGS. 21A to 21D, the flow of the process of concentrating the cells according to the example 3 will be explained. First, as shown in FIG. 21A, the switch 104 is closed and an AC voltage is applied to the concentrating electrode 102. Second, as shown in FIG. 21B, the driving mechanism 108 moves the piston-type incubator 101 into the cell suspension vessel 105. The cells 107 are pressed down against the bottom surface of the cell suspension vessel 105 and coagulate thereon, while the medium 106 passes through the through-hole of the concentrating electrode 102 and moves upward. Third, shown in FIG. 21C, the medium 106, which moved upward, is discharged outside from the cell suspension vessel 105 by means of the discharge mechanism 109 and the discharge tube 110. Finally, as shown in FIG. 21D, the switch 104 is opened to return the piston-type incubator 101 back to its original position shown in FIG. 21A by means of the driving mechanism 108. This operation allows for concentrating the cell suspension in the cell suspension vessel 5.

Herein, the gap distance between the concentrating electrodes 102, and the applied voltage and applied frequency are explained.

The electric field intensity E between cell concentrating electrodes is represented by the above formula 9.

Water, which is a principal component of the medium for cell culture, undergoes electrolysis theoretically at 1.23 V; thereby, the applied voltage need be set to 1.23 V or lower. Moreover, as shown in the formula 1, since the dielectrophoretic force is proportional to the applied voltage. At the applied voltage lower than 20 mV, the dielectrophoretic force becomes smaller, namely the force for driving the cells is decreased; accordingly, the applied voltage is preferably equal to or higher than 20 mV.

To manipulate the cells, the electric field intensity E equal to or higher than $1 \times 10^4$ V/m is required, resulting in the gap distance d between the electrodes being equal to or lower than 123 μm. Furthermore, for the animal cells, of which average diameter is 10 μm, the gap distance between the electrodes is preferably within the range from 20 to 30 μm.

The above formula 10 represents the amplitude of the impedance between the aforementioned electrodes.

In the formula, S is the area between the opposing electrodes. As known from the formula 10, assuming that the gap distance d between the electrodes is constant, the larger the applied frequency f, the smaller the impedance. Specifically, when high frequency is applied, the resistance between the electrodes, increasing flowing current. This elevates the medium temperature, causing the environment appropriate for cell culture to be deteriorated or a current control system to be complicated. In addition, considering the technique for achieving a high frequency apparatus, the applied frequency is preferably equal to or lower than 10

MHz. However, with higher electric conductivity of the medium, electrolysis of water occurs even when low-frequency AC voltage is applied; accordingly, the applied voltage is preferably equal to or higher than 100 MHz.

According to the example 3 of the present invention, the cell concentrating apparatus of the present invention is capable of concentrating the cells easily and efficiently by means of dielectrophoretic force, rather than the conventional membrane separation process, centrifuge separation method, and precipitation separation method.

Example 4

Figure 22:
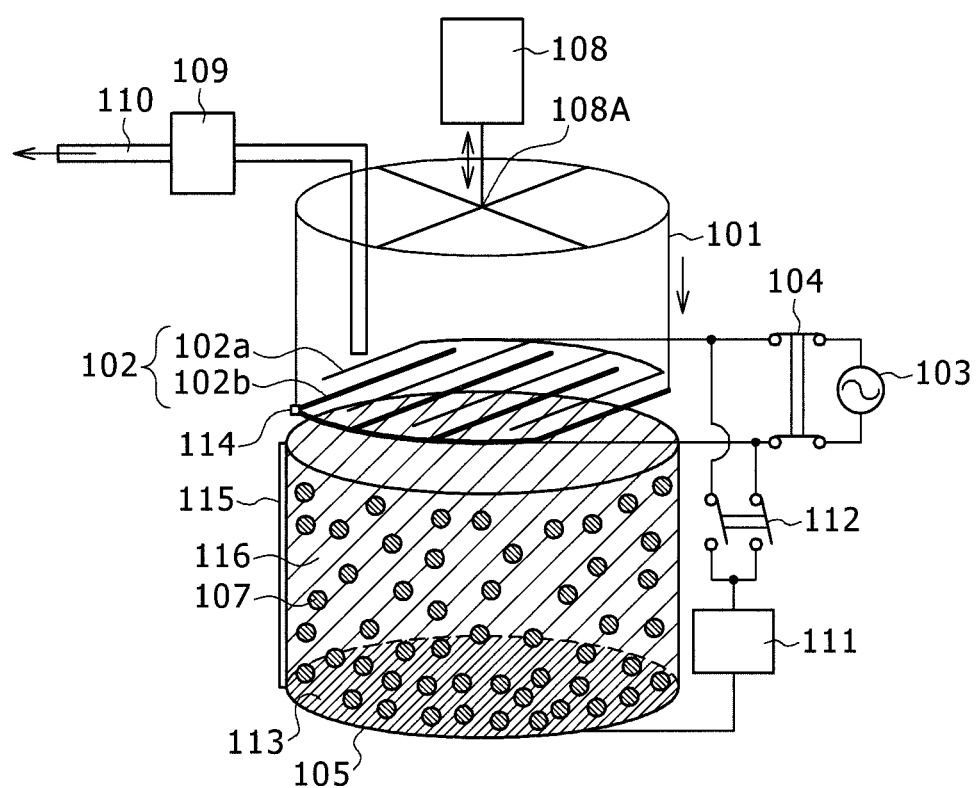
FIG. 22 is a view showing a cell concentration apparatus according to a fourth embodiment of the present invention.

The example 4 of the present invention measures the impedance between the concentrating electrode and the bottom surface electrode of the present invention to determine the cell concentration. The example 4 is explained by reference to FIG. 22. Hereinafter, the same signs are assigned to the same parts as those described in the example 3 to omit their explanation and only the different parts are explained.

113 is a bottom surface electrode disposed on the bottom surface of the cell suspension vessel, 111 is an impedance measuring apparatus electrically connected to the bottom surface electrode 113, and 112 is a switch connecting the concentrating electrode 102 and the impedance measuring apparatus. 114 is a position sensor of the concentrating electrode, and 115 is magnetic sheet for the position sensor.

Figure 23A:
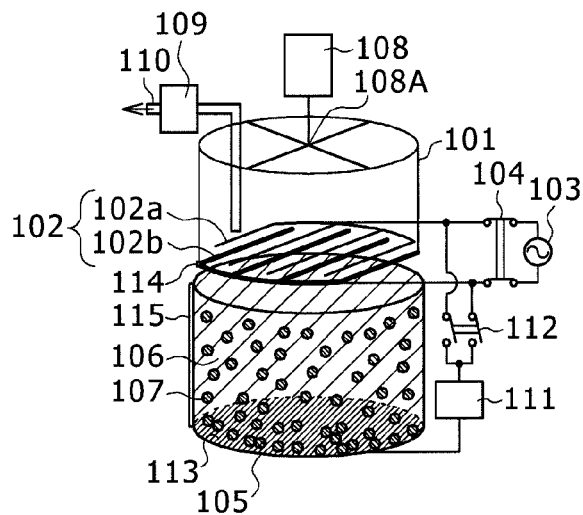
FIG. 23A is a view showing a flow A of concentration measurement at the cell concentration apparatus according to an example 4 of the present invention.
Figure 23B:
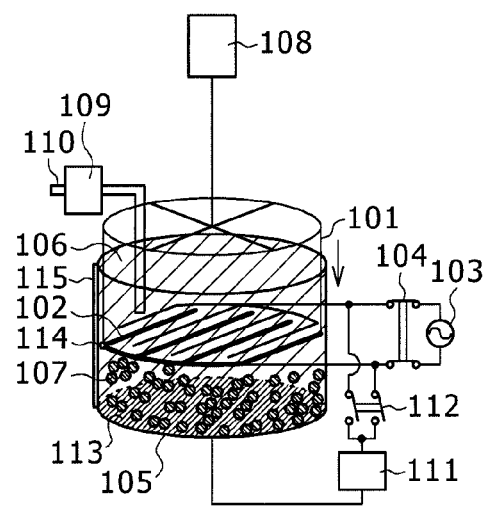
FIG. 23B is a view showing a flow B of concentration measurement at the cell concentration apparatus according to the example 4 of the present invention.
Figure 23C:
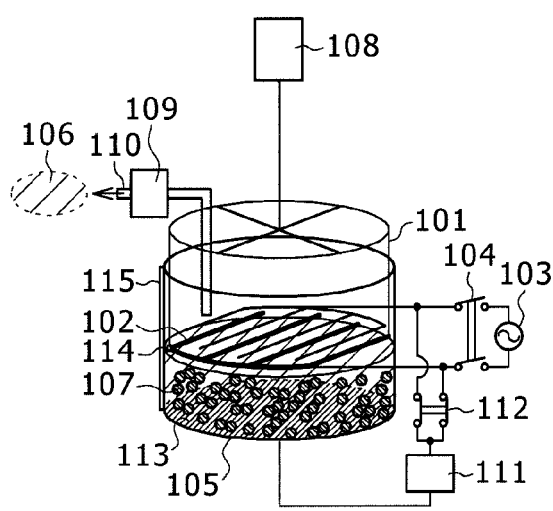
FIG. 23C is a view showing a flow C of concentration measurement at the cell concentration apparatus according to the example 4 of the present invention.
Figure 23D:
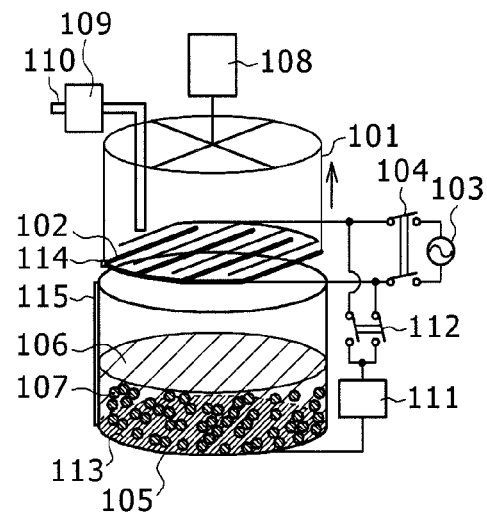
FIG. 23D is a view showing a flow D of concentration measurement at the cell concentration apparatus according to the example 4 of the present invention.

The flow of a process of measuring the cell concentration according to the example 4 of the present invention is explained by reference to FIGS. 23A to 23D. First, as shown in FIG. 23A, the switch 104 is closed and the switch 112 is opened. Second, as shown in FIG. 23B, the driving mechanism 108 moves the piston-type incubator 101 toward the cell suspension vessel 105. The cells 107 are coagulated on the bottom surface of the cell suspension vessel 105 by means of dielectrophoresis, while the medium 106 passes through the through-hole of the concentrating electrode 102 and moves upward. Third, as shown in FIG. 23C, the medium 106, which moved upward, is discharged outside from the cell suspension vessel 105 by means of the discharge mechanism 109 and the discharge tube 110. At this point, the switch 104 is opened and the switch 112 is closed. The impedance measuring apparatus 111 measures the impedance between the concentrating electrode 102 and the bottom surface electrode 113 to estimate the count of the cells contained in the medium. Moreover, the position sensor 114 measures the volume of the cell suspension. This allows for measurement of the concentration of the concentrated cells. Finally, as shown in FIG. 23D, the switch 112 is opened to return the piston-type incubator 101 back to its original position shown in FIG. 23A by means of the driving mechanism 108. This operation allows for concentrating the cell suspension in the cell suspension vessel 105 and measuring the concentration of the concentrated cells.

Herein, the method for determining the cell concentration by measuring the impedance between the concentrating electrode 102 and the bottom surface electrode 113 is explained.

Hereinafter, the impedance Z between the concentrating electrode and the bottom surface electrode is explained by reference to FIG. 24 and the above formulas 4 to 8.

In the formulas, the capacitance is represented by C, the reactance is represented by x, the resistance is represented by r, and the resistor is R.

The formula 4 represents the synthetic impedance Z in the CR parallel equivalent circuit, the formula 5 represents the resistance r in the CR parallel equivalent circuit, the formula 6 represents the reactance x in the CR parallel equivalent circuit, the formula 7 represents the resistor R in the CR parallel equivalent circuit, and the formula 8 represents the capacitance C in the CR parallel equivalent circuit.

Figure 24:
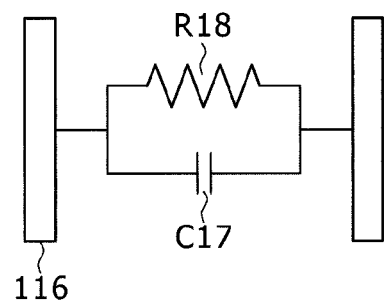
FIG. 24 is a view illustrating an equivalent circuit for a cell disposed between the electrodes.

FIG. 24 shows the electric state between the lower electrodes 116 of the cell culture vessel by means of an equivalent circuit. There exists the medium containing the cells between the electrodes 116. The capacitance (C) 17 configured using the medium as an inter-electrode dielectric and the electroconductive resistor (R) 18 connect in parallel between the electrodes 116 before the cells migrate into the gap between the electrodes.

The medium is homogenous liquid. In contrast, the cell is enclosed with an almost insulating cell membrane and therefore, large differences in capacitance and resistance are observed between the cell and the medium. Specifically, the capacitance and resistance of the medium have been measured in advance and when the cells are seeded in the medium, the cell count is determined based on the changes in capacitance and resistance. Since the impedance may be assessed based on the capacitance and resistance, the cell count may be estimated based on the impedance by assessing, in advance, the relationship between the cell count and the impedance. In other words, the cell count may be estimated based on the impedance between the concentrating electrode and the bottom surface electrode.

Example 5

Figure 25:
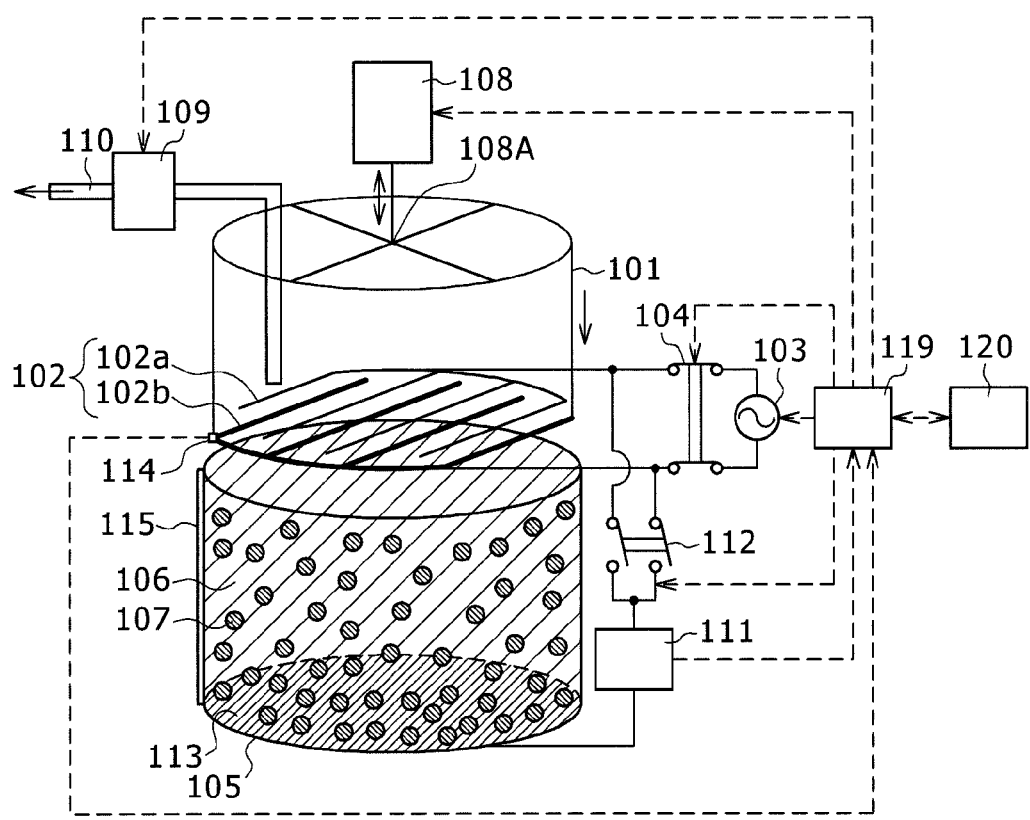
FIG. 25 is a view showing a cell concentration system of an example 5 of the present invention.

By reference to FIG. 25, the cell concentration system according to the example 5 of the present invention.

In FIG. 25, the parts excluding a control processor 119 and a monitor 120 are the same as those explained with respect to the example 4. Note that the broken line in FIG. 25 is an electric signal line connecting the control processor 119 to individual electric control parts.

The cell concentration system shown in FIG. 25 is capable of controlling and monitoring the steps of concentrating the cells and measuring the cell concentration explained above with respect to the example 4. First, the switch 104 is closed and the switch 112 is opened. Second, the driving mechanism 108 moves the piston-type incubator 101 to the cell suspension vessel 105. Third, the medium 106 is discharged outside of the cell suspension vessel 105 by means of the discharge mechanism 109 and the discharge tube 110. At this point, the switch 104 is opened and the switch 112 is closed. The impedance measuring apparatus 111 measures the impedance between the concentrating electrode 102 and the bottom surface electrode 113 to estimate the count of the cells contained in the medium. Moreover, the position sensor 114 measures the volume of the cell suspension. This allows for measurement of concentration of the concentrated cells. Finally, the switch 112 is opened to return the piston-type incubator 101 to its original position by means of the driving mechanism 108. This operation enables the cell suspension contained in the cell suspension vessel 105 to be concentrated and the concentration of the concentrated cells to be measured. At this point, the driving speed of the driving mechanism 108, and the position of the concentrating electrode, the volume of the cell suspension, and cell concentration may be monitored.

Figure 26:
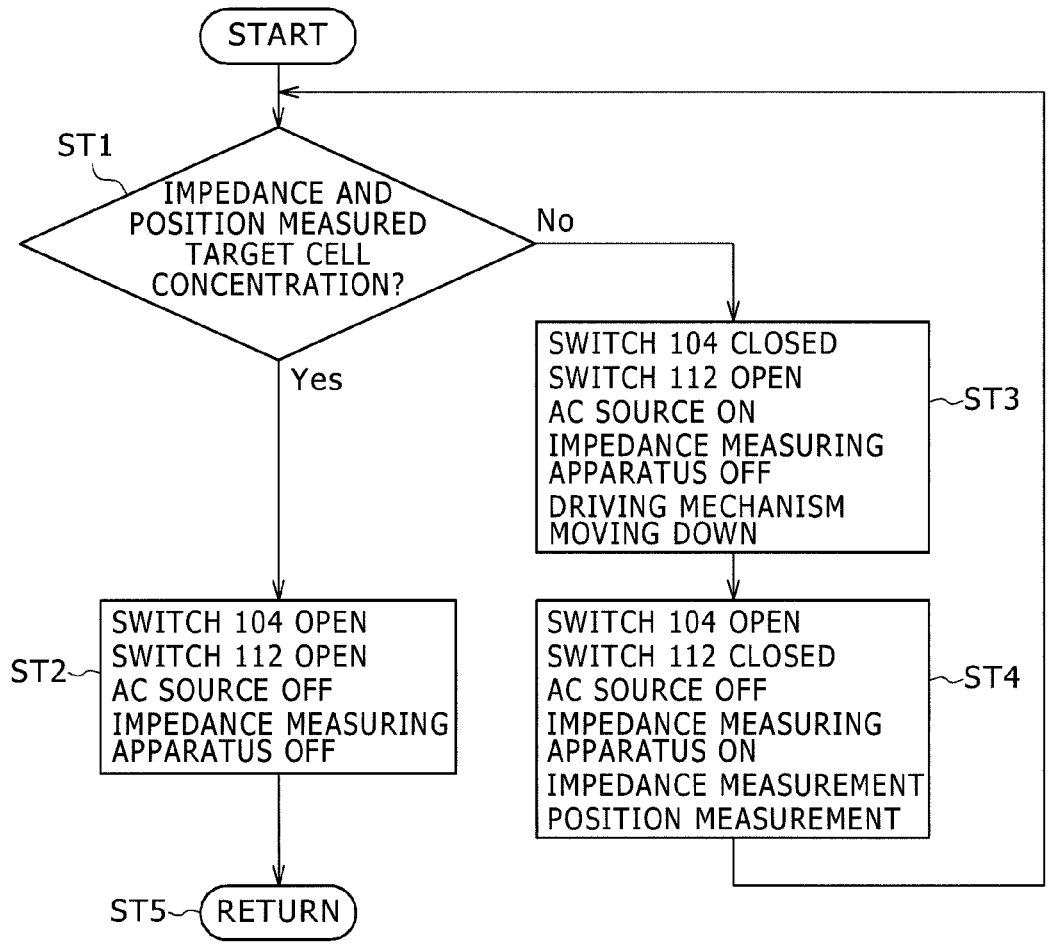
FIG. 26 is a flow sheet illustrating the step of controlling the cell concentration system according to the example 5 of the present invention.

Taking advantage of the above functions, the cells may be concentrated to the target level. The flow sheet of controlling the process is shown in FIG. 26. First, in the first step ST1, it is determined whether or not the cell concentration is the target one. If it is target one, the process goes to the step ST2 for opening the switch 104 and the switch 112. When the step ST2 is finished, control is transferred to the main routine in the step ST5. On the other hand, if the cell concentration is not target one, the process goes to the step ST3 of concentrating the cells contained in the medium by opening the switch 104, turning the AC power source 103 ON, and moving the driving mechanism 108 down. Moreover, the process goes to the step ST4 of opening the switch 104 and closing the switch 112, turning the AC power source OFF and the impedance measuring apparatus 111 ON to measure the impedance and the position. The step ST3 for concentrating the cells to the target cell concentration and the step ST4 of measuring the impedance and the position are repeated until the condition set in the step ST1 is met.

Example 6

Figure 27A:
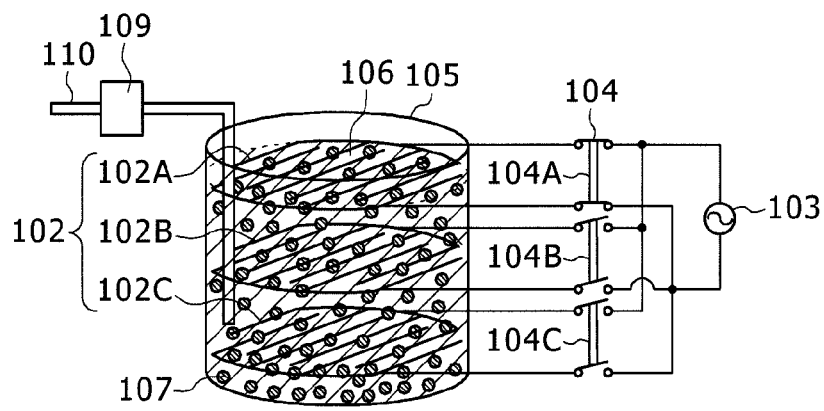
FIG. 27A is a view showing a cell concentration apparatus having a multilayer electrode structure according to an example 6 of the present invention.
Figure 27B:
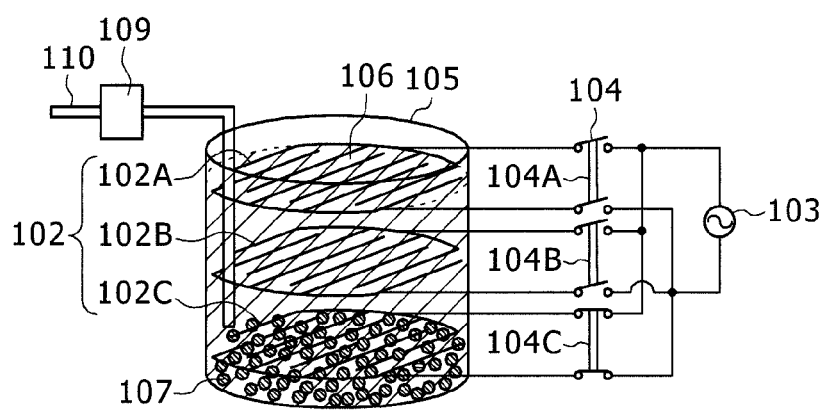
FIG. 27B is a view showing a cell concentration apparatus having a multilayer electrode structure according to the example 6 of the present invention.
Figure 27C:
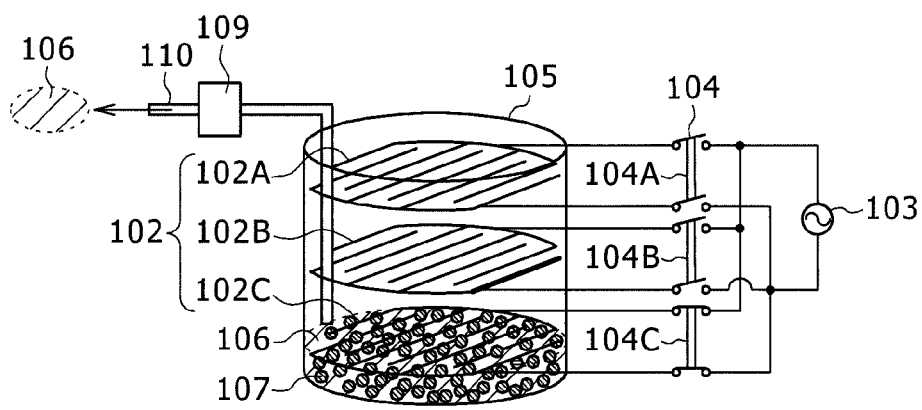
FIG. 27C is a view showing a cell concentration apparatus having a multilayer electrode structure according to the example 6 of the present invention.

A cell concentration apparatus according to the example 6 of the present invention is explained by reference to FIGS. 27A to 27C. Herein after, the same signs are assigned to the same parts as those explained with regard to the examples 3 and 4 to omit the explanation of them and only different parts are explained.

According to the example 6, the concentrating electrode 102 is disposed on the wall of the cell suspension vessel 105 in the form of multi-layer electrodes 102A to 102C. The corresponding one of switches 104A to 104C is disposed between each of the concentrating electrode 102A to 102C and the AC power source 103.

The flow of the process for concentrating the cells according to the example 6 is explained by reference to FIGS. 27A to 27C. First, as shown in FIG. 27A, the switch 104A is closed, the switch 104B is opened, the switch 104C is opened, and an AC voltage is applied to the concentrating electrode 102A to coagulate the cells at the bottom of the concentrating electrode 102A. Second, the switch 104A is opened, the switch 104B is closed, the switch 104C is opened, and an AC voltage is applied to the concentrating electrode 102B to coagulate the cells at the bottom of the concentrating electrode 102B. Third, as shown in FIG. 27B, the switch 104A is opened, the switch 104B is opened, the switch 104C is closed, and an AC voltage is applied to the concentrating electrode 102C to coagulate the cells at the bottom of the concentrating electrode 102C. Finally, as shown in FIG. 27C, the medium 106 on the concentering electrode 102C may be discharged outside of the cell suspension vessel 105 by means of the discharge mechanism 109 and the discharge tube 110. It goes without saying that three-layer concentrating electrode has been explained with regard to the example 6, but a two-layer or four layer or more concentrating electrode may be used.

Focusing on cell concentration, the present invention has been explained. The principle of the apparatus and the system of the present invention may be inversely used to dilute the cell suspension to the target concentration.

As long as the features of the present invention are not lost, the present invention is not limited to the aforementioned embodiments and examples and includes other embodiments, which may be considered within the scope of the technical idea of the present invention.

Hereinafter, the embodiments of the present invention are summarized and recited.

(1) A cell concentration apparatus for concentrating cells contained in a medium, which includes a cell suspension vessel that supports the media containing the cells, a piston-type incubator moving toward the cell suspension vessel, an electrode disposed on the bottom surface of the piston-type vessel, a through-hole, which pierces through the bottom surface of the piston-type incubator disposed between the electrodes, a power source that applies an AC voltage to the electrode, a driving mechanism that moves the piston-type incubator up from and down to the cell suspension vessel, and a discharge mechanism that discharges the medium, which enters the piston-type vessel through the through-hole.

(2) The cell concentrating apparatus described in (1) which is characterized in that the electrode disposed on the bottom surface of the piston-type incubator presses the cells in a cell suspension against the bottom of the cell suspension vessel by means of a diectrophoretic force.

(3) The cell concentrating apparatus described in (1) which further includes an impedance measuring apparatus that measures the impedance between the electrode disposed on the bottom surface of the piston-type incubator and the electrode disposed on the bottom surface of the cell suspension vessel to estimate the count of the cells in the medium based on the measured impedance.

(4) The cell concentrating apparatus described in (3), which further includes a position sensor that measures the position of the electrode, in which it finds the volume of the cell suspension based on the measured electrode position to determine the cell concentration.

(5) The cell concentration apparatus for concentrating the cells contained in the medium, characterized by including a cell suspension vessel that supports the medium contained the cells, a plurality of electrodes disposed on the inner wall of the cell suspension vessel in the multi-layer form, a through-holes formed between the electrodes, a power source that applies an AC voltage to the electrode, a switch that switches among the plurality of electrodes to which the AC voltage is applied, and a discharge mechanism that discharges the medium which enters the cell suspension vessel.

(6) The cell concentrating apparatus described in (5) which is characterized in that the plurality of electrodes disposed on the inner wall of the cell suspension vessel in the multi-layer form presses the cells in the cell suspension against the bottom of the cell suspension vessel by means of a negative dielectrophoretic force.

(7) The cell concentrating apparatus described in any one of (1) to (6) which is characterized in that the voltage applied for generating an electric field between the electrodes is within the range from 20 mV to 1.23 V.

(8) The cell concentrating apparatus described in any one of (1) to (6) which is characterized in that the frequency applied for generating an electric field between the electrodes is within the range from 100 Hz to 10 MHz.

(9) The cell concentrating apparatus described in any one of (1) to (6) which is characterized in that the gap distance between the electrodes is equal to or less than 123 μm.

(10) The cell concentrating apparatus described in any one of (1) to (6) which is characterized in that the electrodes are made of any one of platinum, gold, chrome, palladium, rhodium, silver, aluminum, tungsten, and ITO, or any combination of them.

(11) A cell concentrating system composed of a cell concentrating apparatus described in any one of (1) to (6); and a control processor that controls the individual parts of the cell concentrating apparatus.

(12) A method for concentrating cells using a cell concentrating apparatus described in one of (1) and (2), which includes: supplying a medium containing cells in the cell suspension vessel; moving the piston-type incubator downward while applying an AC voltage to the electrode; and discharging the medium, which enters the piston-type incubator through the through-holes.

(13) A method for concentrating the cells using the cell concentrating apparatus described in (4), which includes: supplying the medium containing the cells in the cell suspension vessel; moving the piston-type incubator downward while applying an AC voltage to the electrode; and discharging the medium, which enters the piston-type incubator through the through-holes; measuring the impedance between the electrode disposed on the bottom surface of the piston-type incubator and the electrode disposed on the bottom surface of the cell suspension vessel using the impedance gauge and finding the volume of the cell suspension using the position sensor; finding the cell concentration based on the measured impedance and volume of the cell suspension; and ending the cell concentration process if the found cell concentration has reached the target level, and going to the step of moving the piston-type incubator downward if it is lower than the target level.

(14) A method for concentrating the cells using the cell concentrating apparatus described in one of (5) and (6), which includes: supplying the medium containing the cells in the cell suspension vessel; switching among the electrodes arranged in the multi-layer form to apply the AC voltage to them sequentially from one end; and discharging the medium, which enters the cell suspension vessel through the through-holes.

Note that according to the above-recited embodiments of the present invention, the cells contained in the medium may be concentrated efficiently with less load on them. The cell concentration may be measured by means of electric signals.

REFERENCE SIGNS LIST

1 . . . Incubator ceiling substrate, 2 . . . Incubator bottom substrate, 3 . . . Upper electrode, 3A . . . Expansion mechanism, 3B . . . Side electrode, 4 . . . Lower electrode, 5 . . . Inside of the incubator, 5A . . . Culture medium, 5B . . . Cell, 6 . . . Medium inlet, 6A . . . Medium inlet valve, 7 . . . Medium outlet, 7A . . . Medium outlet valve, 8 . . . Mixed-gas inlet, 8A . . . Mixed-gas inlet valve, 9 . . . Mixed-gas outlet, 9A . . . Mixed-gas outlet valve, 10 . . . AC power source, 11 . . . Impedance measuring apparatus, 12 . . . DC power source, 13A . . . Switch, 13B . . . Switch, 14 . . . Switching element, 15A . . . Driving circuit, 15B . . . Driving circuit, 15C . . . Driving circuit, 16 . . . Electrode, 17 . . . Capacitance C, 18 . . . Resistor R, 101 . . . Piston-type incubator, 102 . . . Concentrating electrode, 103 . . . AC power source, 104 . . . Switch, 105 . . . Cell suspension vessel, 106. Medium, 107 . . . Cell, 108 . . . Driving mechanism, 108A . . . Support mechanism, 109 . . . Discharge mechanism, 110 . . . Discharge tube, 111 . . . Impedance measuring apparatus, 112 . . . Switch, 113 . . . Bottom surface electrode, 114 . . . Position sensor, 115 . . . Magnetic sheet, 116 . . . Electrode, C17 . . . Capacitance C, R18. Resistor R, 119 . . . Control processor, 120 . . . Monitor.

The invention claimed is:

1. A cell culture device comprising:
a cell culture vessel that supports and cultures cells;
an inlet that supplies a medium to the cell culture vessel and an outlet that discharges a medium from the cell culture vessel; and
a power source that applies a voltage to an electrode disposed in the cell culture vessel,
the cell culture vessel having a space enclosed by a housing that supports a medium, a bottom surface of the space to which cells can attach,
a plurality of first electrodes disposed on the bottom surface of the space, and a second electrode opposed to the first electrodes,
wherein the first electrodes are configured to guide cells contained in the space to the bottom surface of the space and to immobilize them there, and to detach the cells immobilized by the first electrodes,
the power source that includes a first power source that is adapted to apply an AC electric field to two different sets of the plurality of first electrodes in order to generate a heterogeneous electric field in the space for immobilizing the cells, and a second power source that is adapted to apply a DC electric field to the first and second electrodes in order to induce electrolysis in the space for detaching the cells.

2. The cell culture device according to claim 1, wherein the first electrodes are configured to generate a heterogeneous electric field, the heterogeneous electric field composed of a strong electric field and a weak electric field.

3. The cell culture device according to claim 2, wherein the first electrodes are configured to generate the strong electric field and the weak electric field to repeat periodically.

4. The cell culture device according to claim 2, wherein an AC voltage applied to the plurality of first electrodes is within the range from 20 mV to 1.23 V.

5. The cell culture device according to claim 2, wherein a frequency applied to the plurality of first electrodes is within the rage from 100 Hz to 10 MHz.

6. The cell culture device according to claim 2, wherein electrode gaps between the plurality of first electrodes is equal to or less than 123 μm.

7. The cell culture device according to claim 2, wherein the plurality of first electrodes are made of any one of platinum, gold, chrome, palladium, rhodium, silver, aluminum, tungsten, and ITO, or any combination of them.

8. The cell culture device according to claim 1, wherein the first electrodes are configured to immobilize cells by means of a negative dielectrophoretic force provided that a medium exerts the negative dielectrophoretic force on the cells.

9. The cell culture device according to claim 8, wherein the first electrodes are configured to immobilize cells in the weak electric field by means of the negative dielectrophoretic force.

10. The cell culture device according to claim 1, wherein the first and second electrodes are configured to generate a DC electric field to detach cells.

11. The cell culture device according to claim 1, wherein a distribution and growth progress of the cells are determined based on changes in electric signals between the plurality of first electrodes.

12. The cell culture device according to claim 1, further comprising:
a first switch for conducting electricity from the second electrode to the first electrodes through the second power source; and
a second switch for conducting electricity from the first power source to the first electrodes.

* * * * *